(12) United States Patent
Kamal et al.

(10) Patent No.: US 6,441,198 B1
(45) Date of Patent: Aug. 27, 2002

(54) PODOPHYLLOTOXIN DIMER AS DNA TOPOISOMERASE II INHIBITORS, AND A PROCESS FOR THE PREPARATION THEREFORE

(75) Inventors: Ahmed Kamal; Laxman Eltepu; Arifuddin Mohammed; Gollapalli Bhasker Ramesh Khanna, all of Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/747,499

(22) Filed: Dec. 22, 2000

(51) Int. Cl.7 .............................................. C07D 307/77
(52) U.S. Cl. ....................... 549/298; 549/326
(58) Field of Search .................. 549/298, 326

(56) References Cited

U.S. PATENT DOCUMENTS 5,880,131 A * 3/1999 Greenwald et al. ......... 514/279

* cited by examiner

Primary Examiner—Ba K. Trinh

(74) Attorney, Agent, or Firm—Ladas & Parry

(57) ABSTRACT

The present invention discloses novel podophyllotoxin dimers having structural formula I

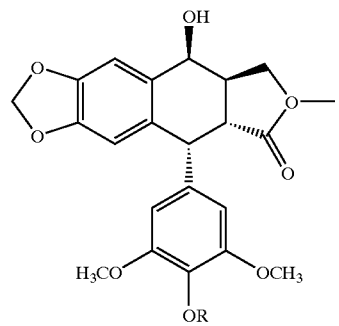

wherein R is H or $CH_3$ and Z is aryl or subsituted aryl compound selected form the group counting of phenylene, naphthalene, p-terpbhnyl, dimethoxy benzidine and diphenyl ether and a process for the preparation of said novel podophyllotoxin dimers. The new podophyllotoxin dimers, pawculaty 4-arylamino derivatives of the podophyllotoxin dimers of the present invention as useful as potent inhibitors of DNA-topoisomerase II and are also useful as antitumour agents.

9 Claims, 1 Drawing Sheet

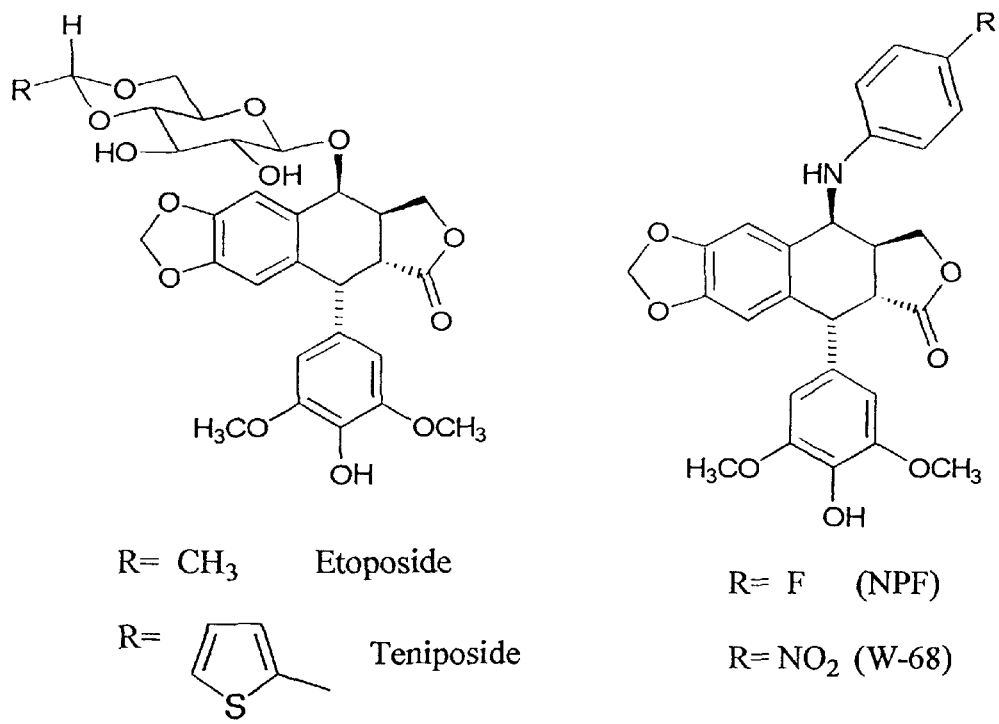
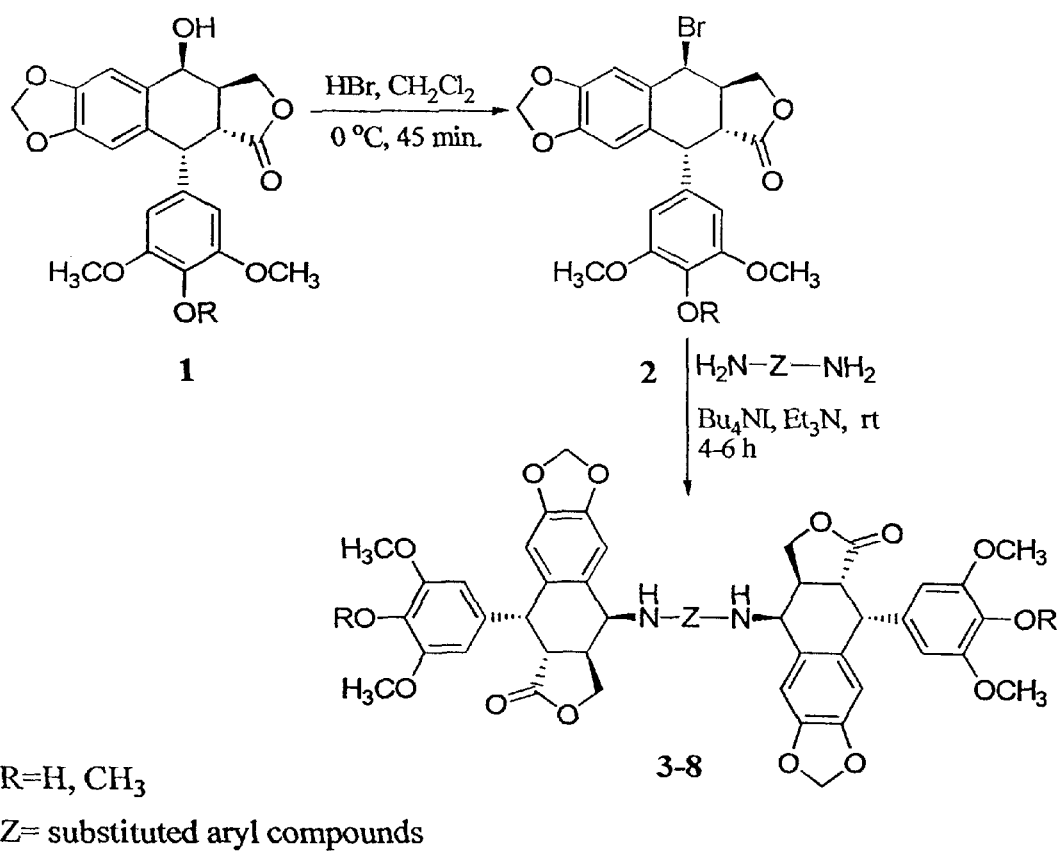
R=H, CH₃
Z= substituted aryl compounds
Figure:1

PODOPHYLLOTOXIN DIMER AS DNA TOPOISOMERASE II INHIBITORS, AND A PROCESS FOR THE PREPARATION THEREFORE

FIELD OF THE INVENTION

The present invention relates to a process for the synthesis of new podophyllotoxin dimers as DNA-topoisomerase II inhibitors.

The present invention particularly relates to the synthesis of a new class of 4β-arylamio dertives of the podophyllotoxin dimers as potent inhibitors of DNA-topoisomerase II and as useful antitumour agents.

BACKGROUND OF THE INVENTION

Podophyllotoxin is a plant toxin that inhibits the assembly of microtubules. It was first isolated from the North American plant *Podophyllum peltatum linnaeus*, commonly known as the American Mandrake or May Apple [Padwyssotzki V. *Arch Exp. Pathol. Pharmakol.* 1880, 13, 29]. The naturally occurring atyltetralin lignans of podophyllotoxin and desoxypodophyllotoxins have been attempted in the treatment of human neoplas. These have been mostly unsuccessful and complicated by side effects such as nausea, vomiting, diarrhea and damage to normal tissues [Jardin, I. Podophylitoxins, in Anticancer Agents Based an Natural Product Models: Casady, J. M.; Douras, J. D.; Eds; Academic Press: New York, 1980, pp,319–351]. Extensive structural modifications of podophyllotoxin ring system have been performed in order to obtain more potent and less toxic anticancer agents, which resulted in the synthesis of etoposide and teniposide. These two semisynthetic glycoside derivatives of podophyllotoxin have been shown to be active in the treatment of a member of cancers including Moms, acute leukemia, cancers of the lung, ovary, test bladder and brain and kaposis sarcoma associated with the acquired immune deficiency syndrome [Sackett. D.L. Podophyllotoxin, Steganacin and Cambratastain Natural Products that Bind at the Colchicine Site of Tubulin, *Pharm. Ther.* 1998, 59, 163–228].

Etoposide (VP-16) is a widely used antineoplastic agent. The mechanism of action of this drug is due to its ability to inhibit the enzyme DNA-topoisomerase It by stabilizing a cleavable enzyme DNA complex in which the DNA is cleaved and covalently linked to the enzyme [Ross, W. Rowe, T.; Glisson, B.; Yalowch J.; and Liu, L. Role of Topoisomerase II in Mediating Podophyllotoxin-Induced DNA Cleavage, *Cancer Res.*; 1984,44: 5857–5860].

The structural modifications of podophyllotoxin and desoxypodophyllotoxin have led to some non-sugar substituted analogues particularly nitrogen containing derivatives as 4β-N-alkylamino/arylamino compounds of 4'-demethylepipodophyllotoxin. These are as active or more active than etoposide in their inhibition of the human DNA topoisomerase II. Amongst these N-linked congeners NPF [4'-0-demethyl-4β-(4"-fluoroanilino)-4-desoxypodophyllotoxin] and W-68 [4'-0-demethyl-4β-(4"-nitroanilino)-4-desoxypodophyllotoxin] have been shown better anticancer activity in their preclinical studies [Zhang, Y. L.; Tropsha, A.; Mephenol, A. T.; Lee, K-H., *J. Med Chem.* 1994, 37, 1460]. NPF is the most active drug which is having 10-fold more potency in inhibiting human DNA topoisomerase II and 113 times more activity in cellular protein-DNA complex formation when compared to etoposide. In the in vitro human tumour cell lines assay, it has proven to be very active.

The structure activity relationship studies, revealed the following features (i) the presence of a 4'-phenolic hydroxyl group.

(ii) maintenance of an intact methylenedioxy system of ring A (iii) the free rotation of E-ring (iv) a —N atom containing at CA4β-position.

The drawbacks of the referred work are that in the treatment of human neoplasia, they have been found to be mostly unsuccessful and complicated by the side effects such as nsea vomiting diarrhea and damage to normal tissues. These significant findings prompted to synthesize a new class of 4-arylnmino derivatives of the podophyllotoxin dimers as potent inhibitors of DNA-topoisomerase II and as useful antitumour agents.

OBJECTS OF THE INVENTION

The main object of the present invention is to provide novel podophyllotoxin dimers as DNA topoisomerase II inhibitors.

Another object of the present invention is provide a process for the synthesis of new podophyllotoxin dimers as DNA topoisomerase II inhibitors, which obviates the drawbacks as detailed above.

Another object of the present invention is to provide a novel and stereo-selective dimers of the podophyllotoxins and 4'-O-demethylepidophyllotoxin in good yields.

Still another object of the present invention is to provide the key step for the synthesis of these dimers by direct nucleophilic substitution of the C-40β-bromo intermediates.

SUMMARY OF THE INVENTION

The above and other objects of the present invention are achieved by providing the new class of C-4β-arylsubstituted N-inked dimers of podophyllotoxin and 4'-O-demethyle pipodophyllotoxins which have been synthesized as DNA-topoisomerase II inhibitors shown in FIG. 1 of the accompanying drawings.

Accordingly, the present invention provides Novel podophyllotoxin dimers having structural formula 3–8.

3-8

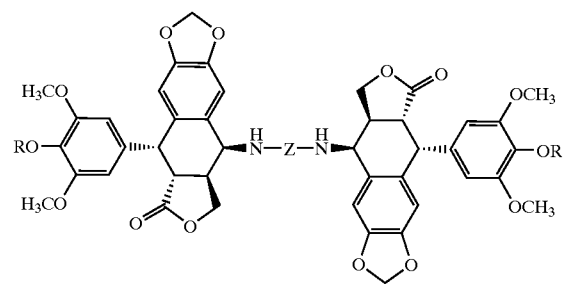

wherein R is H or CH$_3$ and Z is an aryl or substituted aryl compound selected from the group consisting of phenylene, naphtlalene, p-terphenyl dimethoxy benzidine and diphenyl ether.

The present invention also provides a process for preparing new podophyllotoxin dimers as claimed in claim 1, said process comprising (a) stirring a solution of aromatic diamine, a base and a phase transfer catalyst in a dry organic solvent at temperature in the range of −10 to 30° C.;

(b) adding slowly 4β-bromo podophyllotoxin to the above solution;

(c) stirring the above reaction mixture continuously for a time period ranging between 6 to 12 hrs;

(d) evaporating the solvent by known methods; and (e) dissolving the residue in a polar solvent followed by washing and separating the product by conventional methods.

BRIEF DESCRIPTION OF THE ACCOMPANYING DRAWINGS

FIG. 1 discloses the process for the synthesis of new podophyllotoxin dimers as DNA—topoisomerase II inhibitors producing the novel and stereo-selective dimers of the podophyllotoxin in good yields.

DETAILED DESCRIPTION

The process for the synthesis of new podophyllotoxin dimers as DNA-topoisomerase II inhibitors produces the novel and stereo-selective dimers of the podophyllotoxin in good yields, wherein, the key step for the synthesis of these dimers is by direct nucleophilic substitution of C-4β-bromo intermediates, 4β-bromo-podophyllotoxin and 4'-O-demethyl-4β-bromo podophyllotoxin, which have been reacted with diamino aryl compounds with or without substitution in a stereo-selective manner to afford the 4β-N-linked dimers of podophyllotoxin (FIG. 1).

These bromo intermediates have been prepared by the bromination of the related podophyllotoxin compounds as described in the literature [Kuhn, M.; Keller-Juslen, C.; Van wartburg, A Helv. Chemica Acta., 1969, 52, 944].

In an embodiment of the present invention the naturally occurring podophyllotoxin lining was isolated from *Podophyllum peltatum linnaeus*.

In another embodiment of the present invention the synthesis of 4β-bromo intermediates were carried out from bromination of podophyllotoxin and 4'-O-demethylepipodophyllotoxin.

In yet another embodiment of the present invention different unsubstituted and substituted diamino aryl compounds in 0.3 eq to 0.5 eq was used.

In still another embodiment of the present invention a variety of solvents were used for the nucleophilic substitution step, such as dichloromethane, chloroform, tetrahydrofuran and benzene.

In still yet another embodiment of the present invention the catalytic amount of $Bu_4N^+I^-$ was used (0.5 eq–1.0 eq) by strring the reaction mixture between $-10°$ C. to room temperature for 6 to 12 h In still another embodiment of the present invention bases like $K_2CO_3$, $BaCO_3$, $Et_3N$ were used.

In still another embodiment of the present invention the purification of dimers was done by column chromatography using chloroform/methanol, ethylacetate/hexane, and chloroform/acetone/ethylacetate etc.

Thus the present invention provides a new class of podophyllotoxin dimers have been synthesized in a stereo-selective manner.

The following examples are given by way of illusions and therefore should not be construed to limit the scope of the invention

EXPERIMENTAL

TYPICAL PROCEDURE

Preparation of C4β-bromo/4'O-demethyl podophyllotoxin: Hbr was passed through a solution of podophyllotoxin (414 mg, 1 mmol) or 4'-O-demethyl podophyllotoxin (400mg, 1 mmol) in dichloromethane (20 ml) at 0° C. for 45 minutes. After the completion of reaction, the solvent was evaporated in vacuum, which was then used for the next reaction with aryl amines without further purification

EXAMPLE 1

1",4"-[Bis-(4β-N-podophyllotoxin)] phenylene diamine (3a): To a stirred solution of 1,4-phenylene diamine (54 mg, 0.5 mmol), $Et_3N$ (150 mg, 1.5 mmol) and $Bu_4N^+I^-$(185 mg, 0.5 mmol) in dry THF (10 ml) at room temperature, a solution of 4β-bromo podophyllotoxin (476 mg, 1.0 mmol) in THF (20 ml) was added slowly at room temperature under nitrogen atmosphere. The stirring was continued for 6 hr. After completion of the reaction, as indicated by TLC, the THF was evaporated under reduced pressure. The residue was dissolved in the chloroform and washed with water. This was then subjected to column chromatography on silicagel using chloroform: acetone: ethylacetate (9.5: 0.5: 0.5) as eluents to the pure dimer in 80% yield.

Spectral data: $^1H$ NMR(CDCl$_3$); 6.78 (S. 2H), 6.50 (S, 2H), 6.32–6.45 (d, 4H), 6.26 (S, H) 5.90–6.00 (ABq, 4H), 4.50–4.61 (br, 4H), 4.28–4.40 (d, 2H), 3.98–4.10 (t, 2H), 3.80 (d, 18H), 3.40–3.60 (br,2H), 3.07–3.22 (dd, 2H), 2.82–3.05 (m, 2H); FAB (M+) mp. 197–199° C.

EXAMPLE 2

1",5"-[Bis-(4β-N-podophyllotoxin)] naphthalene diamine (4a) was prepared according to the method described for the compound 3a, employing the 1,5-diamino naphthalene (80 mg, 0.5 mmol), $Bu_4N^+I^-$(185 mg, 0.5 mmol), $Et_3N$ (150 mg, 1.5 mmol) and 4β-bromopodophyllotoxin (476 mg, 1.0 mmol) to give 4a in the 78% yield.

Spectral data: $^1H$ NMR(CDCl$_3$): 7.33–7.43 (d, 2H), 7.16–7.28 (t, 2H), 6.78 (S, 2H), 6.56–6.63 (d, 2H), 6.53 (S, 2H), 6.33 (S, 4H), 5.90–6.00 (ABq, 4H), 5.49–5.59 (br, 2H,NH), 4.92–5.05 (br, 2H), 4.55–4.64 (d, 2H), 4.34–4.48 (t, 2H), 3.80–4.93 (t, 2H), 3.75 (S, 18H), 3.49–3.65 (dd, 2H), 2.95–3.10 (m, 2H); FAB MS: m/z 951 ($M^{+1}$); mp. 227–230° C.

EXAMPLE 3

4",-4'"-[Bis-(4β-N-podophyllotoxin)1-p-terphenyl diamine (5a) was prepared according to the method described earlier, employing 4,4'-diamino-p-terphenyl (130 mg, 0.5 mmol), $Bu_4N^+I^-$(185 mg, 0.5 mmol), $Et_3N$ (150 mg, 1.5 mmol) and bromo podophyllotoxin (476 mg, 1.0 mmol) to give the product in 75% yield. Spectral data: $^1$HNMR (CDCl$_3$); 7.63 (d, 4H), 7.50–7.58 (d, 4H), 6.88 (S, 2H), 6.62–6.72 (d, 4H), 6.60 (S, 2H), 6.37 (S, 4H), 6.00–6.08 (ABq, 4H), 4.78 (br, 2H), 4.62–4.70 (d, 2H), 4.42–4.53 (t, 2H), 4.03–4.18 (t, 2H), 3.92–4.09 (d, 2H), 3.86 (d, 18H), 3.16–3.28 (dd, 2E), 2.97–3.13 (m,2H); FAB MS: m/z 1052 ($M^+$); mp. 203–206° C.

EXAMPLE 4

3",-3'"-[Bis-(4β-N-podophyllotoxin)]diamino dinethoxy benzidine (6a) was prepared by the same procedure described earlier using 3,3' diaminoss-dimethoxy benzidine (122 mg, 0.5 mmol) $Bu_4N^+I^-$(185 mg, 0.5 mmol), $Et_3N$ (150 g, 1.5 mmol) and 4β-bromo podophyllotoxin (476 mg, 1.0 mmol) to give the product in 78% yield. Spectral data: $^1H$ NMR (CDCl$_3$); 6.98–7.05 (d, 2H), 6.94 (S, 2H), 6.78 (S, 2H), 6.55 (S, 2H), 6.45–6.52 (d, 2H), 6.32 (S,4H) 5.99 (ABq, 4H), 4.70 (br, 2H), 4.60–4.67 (d, 2H), 4.34–4.49 (t, 2H), 4.00 (t, 2H), 3.93 (S,6H), 3.80 (d, 18H), 3.13–3.28 (dd, 2H), 2.90–3.12 (m, 2H); FAB MS: m/z 1036 (M$^+$); mp. 204–207° C.

EXAMPLE 5

4",4'"-[Bis-(4β-N-podophyllotoxin)] diamino diphenylether (7a) was synthesized by the method described for earlier compounds employing, 4,4'-diamino diphenylether (100 mg, 0.5 mmol), bromopodophyllotoxin (476 mg, 1.0 mmol) Bu$_4$N$^-$(185 mg, 0.5 mmol) and Et$_3$N (150 mng, 1.5 mmol) to give 7a in 78% yield. Spectral data: $^1$H NMR (CDCl$_3$); 6.81–6.90 (d, 4H), 6.79 (S, 2H), 6.49–6.53 (d, 4H), 6.47 (S, 2H), 6.29 (S, 4H), 5.95–6.00 (ABq, 4H), 4.56–4.63 (d, 4H), 4.34–4.45 (t, 2H), 3.98–4.10 (t, 2H), 3.74–3.82 (d, 18H), 3.67–3.72 (d,2H), 3.10–3.21 (dd, 2H), 2.91–3.07 (m, 2H); FAB MS: m/z 993 (M$^{+1}$); mp. 201–204° C.

EXAMPLE 6

2",7"-[Bis-(4β-N-podophyllotoxin)] diaminoflourene (8a) was prepared by the same method described earlier, employing 2,7-diamino flourene (135 mg, 0.5 mmol), Bu$_4$N$^{+/-}$(185 mg, 0.5 mmol) and Et$_3$N (150 mg, 1.5 mmol) and 4β-bromo podophyllotoxin (476 mg, 1.0 mmol) to give 8a in 75% yield. Spectral data: $^1$H NMR (CDCl$_3$); 7.39–7.50 (d, 2H), 6.82 (S, 2H), 6.68 (S, 2H), 6.45–6.58 (br, 4H), 6.31 (S, 4H), 5.92–6.01 (ABq, 4H), 4.71 (br, 2H), 4.60 (d, 2H), 4.38–6.01 (t, 2H), 4.00–4.13 (t, 2H), 3.80 (d, 18H), 3.10–3.22 (dd, 2H), 2.90–3.10 (m 2H); FAB MS: mn/z 988 (M$^+$); mp. 215–218° C.

EXAMPLE 7

1",4"-Bis-(4'-O-demethyl-4β-N-4-desoxypodophyllootoxin)] Phenylene diamine (3b) was synthesized by the procedure described for earlier compounds, employing 1,4-phenylene diamine (54 mg, 0.5 mmol), Bu$_4$N$^+$I$^-$(185 mg, 0.5 mmol), Et$_3$N (150 mg, 1.5 mmol), and 4'-O-demethyl-4β-bromo-4-desoxy-podophyllotoxin (462 mg, 1.0 mmol) to give the product in 76% yield. Spectral data: $^1$H NMR (CDCl$_3$); 6.72–6.85 (m, 4H), 6.46 (S,2H), 6.36 (S, 2H 6.22–6.30 (S, 4H), 5.88–5.98 (ABq. 4H), 5.34 (S, 2H), 4.52 (br, 2H), 4.20–4.40 (t, 2H), 3.90–4.10 (t,2H), 3.75 (S, 6H), 3.16–3.35 (m, 4H); FAB MS: m/z 872(M$^+$); mp. 216–219° C.

EXAMPLE 8

1",5"-[Bis-(4'-O-demethyl-4β-N-4-desoxypodophyllotoxin)] naphthalene diamine (4b) was prepared according to the method described earlier, employing 1,5-diamino naphthalene (80 mg, 0.5 mmol), Bu$_4$N$^{30}$I$^-$(185 mg, 0.5 mmol), Et$_3$N (150 mg, 1.5 mmol) and 4'-O-demethyl-4β-bromo-4-desoxy podophyllotoxin (462 mg, 1.0 mmol) to give the product in 76% yield. Spectral data: $^1$H NMR (CDCl$_3$); 7.22–7.28 (d, 2H), 7.10–7.19 (t, 2H), 6.73 (S, 2H), 6.58 (S, 2H), 6.50 6.55 (d, 2H), 6.33 (S, 4H), 5.98 (ABq, 4H), 5.34 (S, 2H), 4.87 (br, 2H), 4.63–4.70 (d, 2H), 4.52–4.59 (d, 2H), 4.36–4.48 (t, 2H), 3.85–3.95 (d, 2H), 3.82 (3, 6H), 3.20–3.31(dd, 2H), 2.98–3.16 (m, 2H); FAB MS: m/z 922 (M$^+$); mp. 238–240° C.

EXAMPLE 9

4",4'"-[Bis-(4"-O-deimthyl4β-N4-desoxypodophyllotoxin)]-p-terphenyl diamine (5b) was prepared according to the method described earlier, employing 4,4'-diamino-p-terphenyl (130 mg, 0.5 mmol), Bu$_4$N$^+$I$^-$(185 mg, 0.5 mmol), Et$_3$N (150 m 1.5 mmol) and 4'-O-diemthyl-4β-bromo podophyllotoxin (462 mg, 1.0 mmol) to give the product in 72% yield. Spectral data: $^1$H NMR (CDCl$_3$); 7.57 (S, 4H), 7.42–7.52 (s, 4H), 6.81 (S, 2H), 6.58–6.67 (d, 4H), 6.55 (S, 2H), 6.32 (S, 4H), 5.98 (Abq, 4H), 5.35 (S, 2H), 4.70–4.78 (br, 2H), 4.60 (d, 2H), 4.35–4.48 (t, 2H), 4.00–4.11 (t,2H), 3.90 (br, 2H) 3.82 (S, 6H), 3.10–3.21 (dd, 2H), 2.94–3.08 (m, 2H); FAB MS: m/z: 1024(M$^+$); mp. 226–229° C.

EXAMPLE 10

3",3'"-[Bis-(4'-O-demethyl-4β-N-4-desoxypodophyllotoxin)] dimethoxy benzidine (6b) was prepared according to the method described for earlier compounds, employing 3,3'-dimethoxy benzidine (122 mg, 0.5 mmol), Bu$_4$N$^+$I$^-$(185 mg, 0.5 mmol), Et$_3$N (150 mg, 1.5 mmol) and 4'-O-demethyl-4β-bromo podophyllotoxin (462 mg, 1.0 mmol) to give the product in 70% yield. Spectral data: $^1$H NMR (CDCl$_3$) 7.00–7.08 (d, 2H), 6.97 (S, 2H), 6.81 (S, 2H), 6.58 (S, 2H), 6.49–6.55 (d, 2H), 6.36 (S, 4H), 6.01 (ABq, 4H), 5.40 (S, 2H), 4.73 (br, 2H), 4.62–4.68 (d, 2H), 4.37–4.50 (m, 4H), 4.00–4.10 (t, 2H), 3.95 (S, 6H), 3.84 (S, 6H), 3.18–3.30 (dd, 2H), 2.98–3.15 (m, 2H); FAB MS: m/z 1008 (M$^+$); mp.215–218° C.

EXAMPLE 11

4",4'"-[Bis-(4'-O-demethyl-4β-N-4-desoxypodophyllotoxin)] diamino diphenylether (7b) was prepared by the same procedure described earlier, employing 4,4'-diamino diphenylether (100 mg, 0.5 mmol), Bu$_4$N$^+$I$^-$(185 mg, 0.5 mmol), Et$_3$N (150 mg, 1.5 mmol) and bromo compound (462 mg, 1.0 mmol) to give the product in 75% yield. Spectral data: $^1$H NMR (CDCl$_3$); 6.85–6.95 (d, 4H), 6.81 (S, 2H), 6.55 (S, 2H), 6.48–6.54 (d, 4H), 6.34 (S, 2H), 6.01 (ABq. 4H), 5.39 (S, 2H), 4.59–4.69 (m, 4H), 4.35–4.45 (t, 2H), 4.00–4.12 (t, 2H), 3.86 (S, 6H), 3.68–3.76 (d,2H), 3.11–3.23 (dd, 2H), 2.94–3.10 (m, 2H); FAB MS: m/z 964 (M$^+$); mp. 217–219° C.

EXAMPLE 12

2",7"-[Bis-(4'-O-demethylA4β-N-4-desoxypodophyllotoxin)] diamino flourene (8b) was prepared according to the procedure described for the earlier compounds, employing 2,7-diamino flourene (135 mg, 0.5 mmol), Bu$_4$N$^+$I$^-$(185 mg, 0.5 mmol), Et$_3$N (150 mg, 1.5 mmol) and 4'-O-demethyl-4β-bromo podophyllotoxin (462 mg, 1.0 mmol) to give the product in 70% yield. Spectral data: $^1$H NMR (CDCl$_3$); 7.39–7.45 (d, 2H), 6.78 (S, 2H), 6.66 (S, 2H), 6.50 (S, 2H), 6.43–6.48 (d, 2H), 6.30 (S, 4H), 5.92–6.00 (ABq, 4H), 5.33 (S, 2H), 4.70 (br, 2H), 4.55–4.61 (d, 2H), 4.33 4.45 (t, 2H), 3.97–4.10(t,2H), 3.79 (S, 6H), 3.08–3.20 (dd, 2H), 2.90–3.08 (m, 2H); FAB MS: m/z 960 (M$^+$); mp. 240–243° C.

In conclusion, the main advantages of the present inventions are.

1. A new class of podophyllotoxin and 4'-O-demethylepipodophyllotoxin diners have been synthesized as DNA-topoisomerase II inhibitors.
2. These novel dimers have been synthesized in good yields and high stereoselective manner.

We claim:
1. A podophyllotoxin dimer having structural formula 3–8

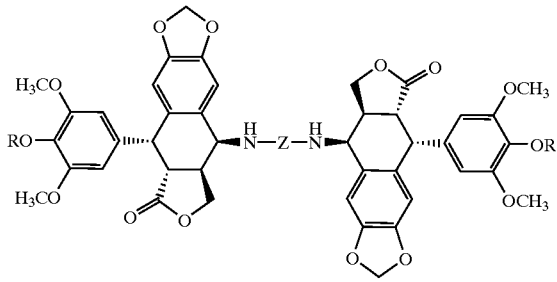

wherein R is H or CH$_3$ and Z is an aryl or substituted aryl compound selected from the group consisting of phenylene, naphthalene, p-terphenyl, dimethoxy benzidine and diphenyl ether.

2. A process for preparing a podophyllotoxin dimer as claimed in claim 1, said process comprising
   (a) stirring a solution of aromatic diamine, a base and a phase transfer catalyst in a dry organic solvent at temperature in the range of 10 to 30° C.;
   (b) adding slowly 4p bromopodophyllotoxin to the above solution;
   (c) stirring the above reaction mixture continuously for a time period ranging between 6 to 12 hrs;
   (d) evaporating the solvent by known methods; and
   (e) dissolving the residue in a polar solvent followed by washing and separating the product by conventional methods.

3. A process as claimed in claim 2 wherein the aromatic diamine used are selected from the group consisting of 1,4 phenylene diamine, 1,5, diamino naphthalene, 4,4'-diatnino-p-terphonyl, 3,3'-diamino dimethoxy benzidine, 4,4'-diamino diphenyl ether and 2,6 diamino fluorene.

4. A process as owmed in claim 2 wherein the organic solvent used is selected from the group consisting of dichloromethane, chloroform, benzene and tetrahydorfuran.

5. A process as claimed in claim 2 wherein base used is selected for K$_2$CO$_3$, BaCO$_3$ and Et$_3$N.

6. A process as claimed in 2, wherein the phase transfer catalyst used is selected from Bu$_4$N$^+$Br$^-$ and Bu$_4$N$^+$I$^-$.

7. A process as claimed in claim 2, wherein the reaction was maintained at –10° C. to room temperature.

8. A process as claimed in claim 2 wherein the stinting was continued for 6 to 12 h.

9. A process as claimed in claim 2 wherein said column chromatography is carried out using chloroform/methanol, ethylacetate/hexane or chloroform/acetonelethylacetate systems as eluents.

* * * * *